United States Patent
Chen et al.

(10) Patent No.: US 8,240,190 B2
(45) Date of Patent: Aug. 14, 2012

(54) AMBIENT-TEMPERATURE GAS SENSOR

(75) Inventors: Junhong Chen, Kenosha, WI (US); Ganhua Lu, Milwaukee, WI (US)

(73) Assignee: UWM Research Foundation, Inc., Milwaukee, WI (US)

(*) Notice: Subject to any disclaimer, the term of this patent is extended or adjusted under 35 U.S.C. 154(b) by 702 days.

(21) Appl. No.: 12/199,891

(22) Filed: Aug. 28, 2008

(65) Prior Publication Data

US 2009/0084163 A1     Apr. 2, 2009

Related U.S. Application Data

(63) Continuation-in-part of application No. 11/508,687, filed on Aug. 23, 2006.

(60) Provisional application No. 60/710,642, filed on Aug. 23, 2005, provisional application No. 61/088,597, filed on Aug. 13, 2008.

(51) Int. Cl.
*G01N 7/00* (2006.01)
(52) U.S. Cl. .......................... 73/31.06; 73/23.2
(58) Field of Classification Search .............. 73/31.06, 73/23.2
See application file for complete search history.

(56) References Cited

U.S. PATENT DOCUMENTS

| 5,460,701 | A | 10/1995 | Parker et al. |
|---|---|---|---|
| 5,514,349 | A | 5/1996 | Parker et al. |
| 5,788,738 | A | 8/1998 | Pirzada et al. |
| 5,851,507 | A | 12/1998 | Pirzada et al. |
| 5,874,684 | A | 2/1999 | Parker et al. |
| 5,905,000 | A | 5/1999 | Yadav et al. |
| 5,939,146 | A | 8/1999 | Lavernia |
| 5,952,040 | A | 9/1999 | Yadav et al. |
| 5,984,997 | A | 11/1999 | Bickmore et al. |
| 5,989,648 | A | 11/1999 | Phillips |
| 6,113,795 | A | 9/2000 | Subramaniam et al. |
| 6,228,904 | B1 | 5/2001 | Yadav et al. |
| 6,254,940 | B1 | 7/2001 | Pratsinis et al. |
| 6,268,054 | B1 | 7/2001 | Costantino et al. |
| 6,379,419 | B1 | 4/2002 | Celik et al. |
| 6,447,848 | B1 | 9/2002 | Chow et al. |
| 6,528,020 | B1 | 3/2003 | Dai et al. |
| 6,528,029 | B1 | 3/2003 | Dettling et al. |
| 6,548,171 | B1 | 4/2003 | Barbera-Guillem et al. |
| 6,623,559 | B2 | 9/2003 | Huang |

(Continued)

FOREIGN PATENT DOCUMENTS

WO      01/44796      6/2001

OTHER PUBLICATIONS

United States Patent Office Action for U.S. Appl. No. 11/508,687 dated Dec. 10, 2010 (25 pages).

(Continued)

*Primary Examiner* — Hezron E Williams
*Assistant Examiner* — Rodney T Frank
(74) *Attorney, Agent, or Firm* — Michael Best & Friedrich LLP (57) ABSTRACT

The invention provides a novel method for the fabrication of nanomaterials, especially nanostructures arranged on a substrate with nanoparticles deposited thereon. The methods of the present invention can be used to fabricate a novel ambient-temperature gas sensor that is capable of detecting a variety of specific gasses over a range of concentrations.

25 Claims, 7 Drawing Sheets

U.S. PATENT DOCUMENTS

| | | | |
|---|---|---|---|
| 6,652,967 | B2 | 11/2003 | Yadav et al. |
| 6,726,992 | B1 | 4/2004 | Yadav et al. |
| 6,730,537 | B2 | 5/2004 | Hutchison et al. |
| 6,765,949 | B2 | 7/2004 | Chang |
| 6,777,639 | B2 | 8/2004 | Schroder et al. |
| 6,855,426 | B2 | 2/2005 | Yadav |
| 6,872,971 | B2 | 3/2005 | Hutchinson et al. |
| 6,933,331 | B2 | 8/2005 | Yadav et al. |
| 7,012,214 | B2 | 3/2006 | Schroder et al. |
| 7,126,081 | B2 | 10/2006 | Schroder et al. |
| 7,172,790 | B2 | 2/2007 | Koulik et al. |
| 7,223,444 | B2 | 5/2007 | Deppert et al. |
| 7,232,771 | B2 | 6/2007 | Jacobs et al. |
| 7,318,908 | B1 | 1/2008 | Dai |
| 7,326,954 | B2 | 2/2008 | Wybourne et al. |
| 7,335,908 | B2 | 2/2008 | Samuelson et al. |
| 7,416,699 | B2 | 8/2008 | Dai et al. |
| 7,442,573 | B2 | 10/2008 | Hutchison et al. |
| 7,528,002 | B2 | 5/2009 | Samuelson et al. |
| 7,531,136 | B2 * | 5/2009 | Besnard et al. ............ 422/82.02 |
| 7,955,559 | B2 * | 6/2011 | Joshi et al. ................... 422/68.1 |
| 2002/0016306 | A1 | 2/2002 | Hutchison et al. |
| 2002/0117659 | A1 | 8/2002 | Lieber et al. |
| 2002/0146742 | A1 | 10/2002 | Wybourne et al. |
| 2003/0077625 | A1 | 4/2003 | Hutchison |
| 2003/0102444 | A1 | 6/2003 | Deppert et al. |
| 2003/0147966 | A1 | 8/2003 | Franzen et al. |
| 2003/0230554 | A1 | 12/2003 | Schroder et al. |
| 2004/0018306 | A1 | 1/2004 | Tenne et al. |
| 2004/0052289 | A1 | 3/2004 | Chang |
| 2004/0057896 | A1 | 3/2004 | Kronholm et al. |
| 2004/0065170 | A1 | 4/2004 | Wu et al. |
| 2004/0075464 | A1 | 4/2004 | Samuelson et al. |
| 2004/0105980 | A1 | 6/2004 | Sudarshan et al. |
| 2004/0166673 | A1 | 8/2004 | Hutchison et al. |
| 2004/0178530 | A1 | 9/2004 | Yadav |
| 2004/0202682 | A1 | 10/2004 | Emrick et al. |
| 2004/0221813 | A1 | 11/2004 | Chang |
| 2005/0000950 | A1 | 1/2005 | Schroder et al. |
| 2005/0008861 | A1 | 1/2005 | Yadav et al. |
| 2005/0011431 | A1 | 1/2005 | Samuelson et al. |
| 2005/0061785 | A1 | 3/2005 | Schroder et al. |
| 2005/0147747 | A1 | 7/2005 | Yadav |
| 2005/0181587 | A1 | 8/2005 | Duan et al. |
| 2005/0199861 | A1 | 9/2005 | Wu et al. |
| 2006/0019470 | A1 | 1/2006 | Seifert et al. |
| 2006/0057360 | A1 | 3/2006 | Samuelson et al. |
| 2006/0063299 | A1 | 3/2006 | Hutchison et al. |
| 2006/0081835 | A1 | 4/2006 | Hutchison et al. |
| 2006/0083694 | A1 | 4/2006 | Kodas et al. |
| 2006/0125056 | A1 | 6/2006 | Samuelson et al. |
| 2006/0159596 | A1 | 7/2006 | De La Veaux et al. |
| 2006/0204441 | A1 | 9/2006 | Atala et al. |
| 2006/0204445 | A1 | 9/2006 | Atala et al. |
| 2006/0204539 | A1 | 9/2006 | Atala et al. |
| 2007/0141163 | A1 | 6/2007 | Vitaliano et al. |
| 2007/0193518 | A1 | 8/2007 | Shiina et al. |
| 2007/0262482 | A1 | 11/2007 | Halpap et al. |
| 2007/0272664 | A1 | 11/2007 | Schroder et al. |
| 2008/0142361 | A1 | 6/2008 | Han et al. |
| 2008/0142926 | A1 | 6/2008 | Seifert et al. |

OTHER PUBLICATIONS

Alivisatos, A.P., "Semiconductor clusters, nanocrystals, and quantum dots," Science (1996) 271:933-937.

Banerjee, S. et al., "Synthesis and characterization of carbon nanotube-nanocrystal heterostructures," Nano Lett. (2002) 2:195-200.

Che, G.L. et al., "Carbon nanotubule membranes for electrochemical energy storage and production," Nature (1998) 393:346-349.

Chen, J.H. et al., "A simple and versatile mini-arc plasma source for nanocrystal synthesis," J. Nano Res. (2007) 9(2):203-213.

Chen, J.H. et al., "Model of the negative DC corona plasma: comparison to the positive DC corona plasma," Plasma Chem. Plasma Process. (2003) 23(1):83-102.

Chen, J. et al., "Controlled decoration of carbon nanotubes with nanoparticles," Nanotechnology (2006) 17:2891-2894.

Chen, R.J. et al., "Noncovalent functionalization of carbon nanotubes for highly specific electronic biosensors," Proc. Natl. Acad. Sci. USA (2003) 100(9):4984-4989.

Choi, H.C. et al., "Spontaneous reduction of metal ions on the sidewalls of carbon nanotubes," J. Am. Chem. Soc. (2002) 124:9058-9059.

Collins, P.C. et al., "Engineering carbon nanotubes and nanotube circuits using electrical breakdown," Science (2001) 292:706-709.

Dresselhaus, M.S. et al., "Phonons in carbon nanotubes," Adv. Phys. (2000) 49(6):705-814.

Fu, Q. et al., "Selective coating of single wall carbon nanotubes with thin $SiO_2$ layer," Nano Lett. (2002) 2(4):329-332.

Han, L. et al., "A direct route toward assembly of nanoparticle-carbon nanotube composite materials," Langmuir (2004) 20(14):6019-6025.

Han, W.Q. et al., "Coating single-walled carbon nanotubes with tin oxide," Nano Lett. (2003) 3(5):681-683.

Haremza, J.M. et al., "Attachment of single CdSe nanocrystals to individual single-walled carbon nanotubes," Nano Lett. (2002) 2(11):1253-1258.

Hu, J.T. et al., "Controlled growth and electrical properties of heterojunctions of carbon nanotubes and silicon nanowires," Nature (1999) 399:48-51.

Jacobs, H.O. et al., "Approaching nanoxerography: the use of electrostatic forces to position nanoparticles with 100 nm scale resolution," Adv. Mater. (2002) 14(21):1553-1557.

Jiang, K.Y. et al., "Selective attachment of gold nanoparticles to nitrogen-doped carbon nanotubes," Nano Lett. (2003) 3(3):275-277.

Kneipp, K. et al., "Surface-enhanced and normal Stokes and anti-Stokes Raman spectroscopy of single-walled carbon nanotubes," Phys. Rev. Lett. (2000) 84(15):3470-3473.

Kong, J. et al., "Functionalized carbon nanotubes for molecular hydrogen sensors," Adv. Mater. (2001) 13(18):1384-1386.

Krinke, T.J. et al., "Microscopic aspects of the deposition of nanoparticles from the gas phase," J. Aerosol Sci. (2002) 33(10):1341-1359.

Krinke, T.J. et al., "Positioning of nanometer-sized particles on flat surfaces by direct deposition from the gas phase," Appl. Phys. Lett. (2001) 78(23):3708-3710.

Kuznetsova, A. et al., "Oxygen-containing functional groups on single-wall carbon nanotubes: NEXAFS and vibrational spectroscopic studies," J. Am. Chem. Soc. (2001) 123(43):10699-10704.

Liu, J. et al., "Fullerene pipes," Science (1998) 280:1253-1256.

Liu, J. et al., "Recent advances in methods of forming carbon nanotubes," MRS Bull. (2004) 29:244-250.

Liu, Y-L. et al., "Gas sensing properties of tin dioxide coated onto multi-walled carbon nanotubes," Thin Solid Films (2006) 497:355-360.

Lu, G. et al., "Gas sensors based on tin oxide nanoparticles synthesized from a mini-arc plasma source," J. Nanomatls. (2006) 1-7.

Lu, G. et al., "Toward novel gas sensors based on hybrid nanostructures," Abstract of 2006 MRS Fall Meeting, Boston, MA Nov. 27-Dec. 1, 2006.

Lu, G. et al., "Room temperature gas sensing with $SnO_2$ nanocrystals supported on MWCNTs," Talk at University of Milwaukee on Aug. 28, 2007, 20 pages.

Luo, J. et al., "Thermal activation of molecularly-wired gold nanoparticles on a substrate as catalyst," J. Am. Chem. Soc. (2002) 124(47):13988-13989.

Murray, C.B. et al., "Synthesis and characterization of nearly monodisperse CdE (E=sulfur, selenium, tellurium) semiconductor nanocrystallites," J. Am. Chem. Soc. (1993) 115(19):8706-8715.

Star, A. et al., "Gas sensor array based on metal-decorated carbon nanotubes," J. Phys. Chem. B. (2006).110;21014-21020.

Suehiro, J. et al., "Fabrication of a carbon nanotube-based gas sensor using dielectrophoresis and its application for ammonia detection by impedance spectroscopy," J. Phys. D: Appl. Phys. (2003) 36:L109-L114.

Tang, Z.Y. et al., "One-dimensional assemblies of nanoparticles: preparation, properties and promise," Adv. Mater. (2005) 17:951-962.

Tsai, D.H. et al., "Electrostatic-directed deposition of nanoparticles on a field generating substrate," Nanotechnology (2005) 16:1856-1862.

Yildirim, T. et al., "Titanium-decorated carbon nanotubes as a potential high-capacity hydrogen storage.medium," Phys. Rev. Lett. (2005) 94:175501-175505.

United States Patent Office Action for U.S. Appl. No. 11/508,687 dated May 6, 2010 (24 pages).

United States Office Action for U.S. Appl. No. 11/508,687 dated Jan. 27, 2010 (30 pages).

United States Patent Office Action for U.S. Appl. No. 11/508,687 dated Jul. 23, 2009 (29 pages).

Zhu, L et al., "A generic approach to coat carbon nanotubes with nanoparticles for potential energy applications," Journal of Heat Transfer (2008) 130:044502-1-3.

United States Patent Office Action for U.S. Appl. No. 11/508,687 dated May 24, 2011 (27 pages).

* cited by examiner

AMBIENT-TEMPERATURE GAS SENSOR

CROSS REFERENCE TO RELATED APPLICATIONS

This application is a continuation-in-part of U.S. patent application Ser. No. 11/508,687 filed Aug. 23, 2006, which claims the benefit of priority to U.S. Provisional Patent Application Ser. No. 60/710,642 filed Aug. 23, 2005, and to U.S. Provisional Patent Application Ser. No. 61/088,597 filed Aug. 13, 2008, both of which are incorporated herein by reference in their entirety.

STATEMENT REGARDING FEDERALLY SPONSORED RESEARCH

This invention was made with government support under grant number 0609059 awarded by the National Science Foundation. The U.S. Government has certain rights in the invention.

BACKGROUND OF THE INVENTION

The present invention relates to the assembly of nanomaterials, and, in particular, to a method of using electrostatic force to assemble nanoparticles onto nanostructures. The invention also relates to ambient-temperature gas sensors that can be constructed using the disclosed method of using electrostatic force to assemble nanoparticles onto nanostructures.

The manufacture of nanostructures from carbon nanotubes and nanoparticles may be useful in a broad range of applications including: nanoelectronics, chemical sensors, biosensors, catalysis, fuel cells, and hydrogen storage. Current methods for assembling these components are primarily based on "wet-chemical" techniques in which the components are created or manipulated with chemical reactions taking place in solution. These methods, however, are generally very slow, and the associated interfacial chemistry is material-dependent, limiting their ability to create nanostructures of arbitrary composition. Furthermore, although the size of the nanoparticles may be controlled in the solution prior to assembly, there is very limited control over the assembly process.

SUMMARY

The present invention discloses methods to conveniently and efficiently decorate nanostructures, including both single-walled and multi-walled carbon nanotubes, with nanoparticles by using electrostatic force directed assembly ("ESFDA"). Using ESFDA, the packing density, spacing, and size distribution of nanoparticles on nanostructures can be controlled during the assembly process. Due to the inherent material independent nature of electrostatic force, nanoparticle-nanostructure compositions can be produced from a variety of different materials and different combinations of materials.

Specifically, the present invention provides a method of coating various nanostructures with a variety of nanoparticles thereby imparting unique chemical and/or electrical properties to the nanostructures. In one embodiment, a plurality of charged aerosol nanoparticles is produced, and an electrical field is applied to the nanostructures. The charged nanoparticles are then introduced to the electrical field, are attracted to the nanostructures and deposited on the nanostructures.

In one embodiment, the invention provides a novel sensing device making use of the ability to deposit materials of arbitrary composition, in a regular manner, to a conductive nanostructure. Such a novel sensing device comprises one or more electrodes, formed on a substrate and adapted to be operatively connected to a meter to measure an electrical characteristic between the electrodes, one or more nanostructures in contact with the one or more electrodes, and one or more nanoparticles deposited on the nanostructures. Optimally, the novel sensing device is operative for a temperature range from about 0° C. to about 200° C., and does not require an additional heating element to obtain a linear response to introduced gases. In an alternative embodiment a plurality of ambient-temperature gas sensors may be arranged in an array, and the plurality of ambient-temperature gas sensors may comprise nanoparticles of differing compositions.

Using the novel sensing devices of the invention, it is possible to detect gasses of interest in the ambient air, including, but not limited to, flammable and/or toxic gasses such as $H_2$, $NO_2$, $CO$, $NH_3$, $H_2S$, and $CH_4$. Detecting these gasses comprises the steps of providing a novel sensing device of the invention, introducing a gas, and monitoring a change in one or more electrical characteristics of the novel sensing device as a function of time.

The invention further provides a method for making an ambient-temperature gas sensor, e.g., a gas sensor with a linear response to gasses of interest over a range of temperatures. This method is a further refinement of the ESFDA technique disclosed herein, comprising the steps of contacting one or more electrodes with nanostructures, producing an aerosol of charged nanoparticles, applying an electric potential to the one or more electrodes and nanostructures, interacting the aerosol of charged nanoparticles with the one or more electrodes and the nanostructures, thus causing the nanoparticles to be deposited upon the nanostructures, and operatively connecting the one or more electrodes to a meter, wherein the meter indicates the presence of a gas in contact with the nanoparticles.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any nonclaimed element as essential to the practice of the invention.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein.

One object of the invention is to provide an assembly technique that is largely indifferent to the chemical composition of the nanoparticles and nanostructures, and that, thus, may be used to assemble a variety of novel structures of arbitrary composition. The nanostructures may be either single-walled or multi-walled in nature. The bonding between the nanostructures and nanoparticles may be non-covalent in nature so as to preserve the $sp^2$ hybridization of carbon atoms. It is thus another object of the invention to preserve desirable electronic properties of carbon in the nanostructure.

It is yet another object of the present invention to provide an assembly technique that allows multidimensional control of the assembly process. The assembly time may be controlled so as to control the packing density of nanoparticles on nanostructures. In addition or alternatively, the aerosol flow rate and/or electrical field may also be controlled so as to control the size of the nanoparticles that attach to the nanostructures. The nanostructures used in the invention may be nanotubes, nanorings, nanowires, or nanorods, or other suitable nanocomponent. The nanoparticles introduced to the electrical field may comprise any of a number of known nanoparticle materials, including, but not limited to, Ag, Au, Pd, Pt, Ni, Co, $TiO_2$, ZnO, $SnO_2$, $WO_3$. It is also possible to use a mixture of two or more different types of nanoparticles, thus providing an ability to uniquely engineer nanocomponents with desired electrical and/or chemical properties, including catalytic, photoelectric, and semiconductor properties.

It is thus another object of the invention to provide assembly techniques that allow great flexibility in the types and composition of nanoparticles being used is widely applicable to applications such as: filtration, sensing, purification, generation of materials, catalyzation, hydrogen storage, fuel cell components, discharge electrodes, spintronics, Raman scattering, wave guides, solar energy harvesting, nanometrology, and creating nanocomponents for the study of nanomechanics.

Figures 1, 2:
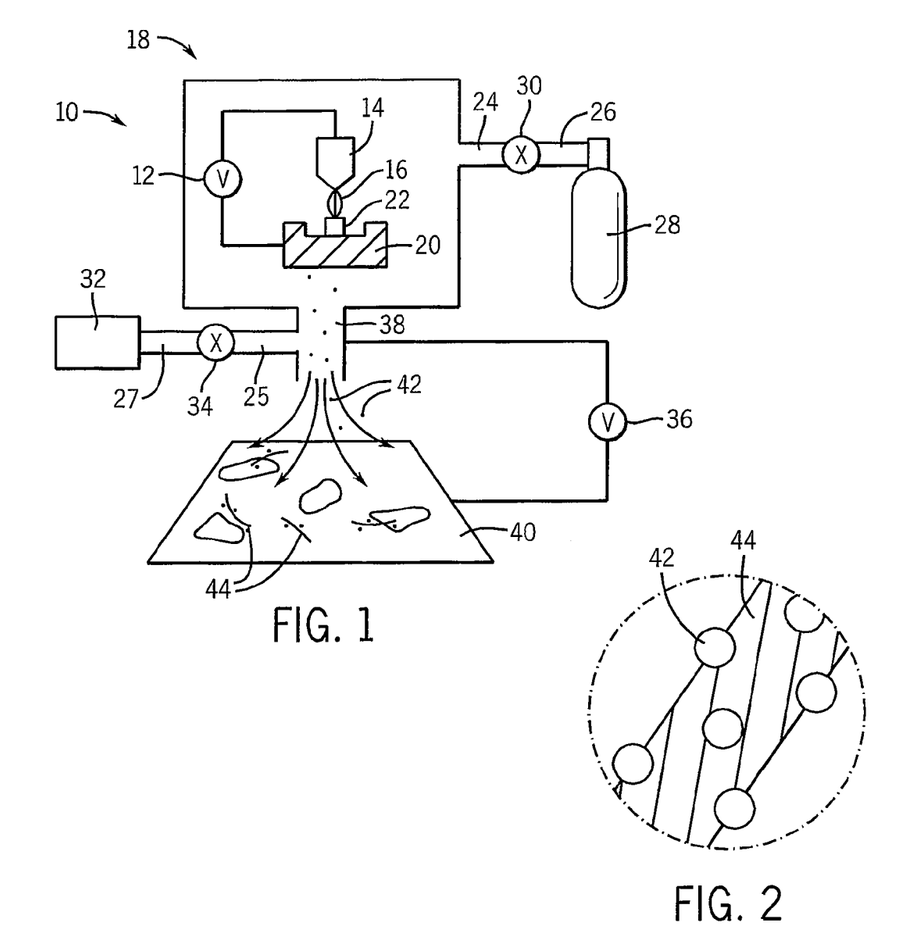
FIG. 1 is a schematic representation of the electrostatic assembly apparatus of the present invention showing a nanoparticle generating arc and a carrier gas system flowing aerosol nanoparticles over a grid of nanotubes charged to attract and bond to the nanoparticles.
FIG. 2 is a simplified depiction of a TEM image of the assembled nanostructures of FIG. 1.

Referring to FIG. 1, an electrostatic force directed assembly (ESFDA) device 10 provides an arc plasma source chamber 18 enclosing an arc cathode 14 opposed to an arc anode 20, the latter holding a precursor material 22 from which nanoparticles will be created. A plasma arc voltage source 12 couples the arc anode 20 to the arc cathode 14 to create the arc 16 which strikes the precursor material 22 for the production of the nanoparticles 42. The arc cathode 14 and arc anode 20 may be, for example, tungsten and graphite respectively.

The application of the arc 16 to the precursor material 22, creates an aerosol of nanoparticles 42 through physical vaporization of the solid precursor material 22. This generation of nanoparticles creates a relatively broad size distribution of nanoparticles 42. A significant fraction of the nanoparticles 42 are charged by the arc 16 or through plasma or thermionic emission, which makes ESFDA feasible without the use of further nanoparticle 42 charging device. The charging of the nanoparticles 42 may prevent their agglomeration. Alternatively, the nanoparticle 42 production means may use aerosol reactors or may aerosolize colloidal nanoparticles 42, in which case additional charging means may be required in such assemblies, or example using corona discharge electrodes.

Multiple precursor materials 22 may be used, for example, silver (Ag) and tin oxide ($SnO_2$) from different arc assemblies or by using a mixture of precursor materials 22. The gaseous aerosol may thus comprise a mixture of different nanoparticles 42, including generally catalysts, photo-catalysts, or semiconductors. The nanoparticles 42 will typically be less than 100 nanometers in diameter and may have a mean diameter of less than 20 nanometers.

The ESFDA device 10 further provides a room temperature carrier gas source 28 that is connected to the plasma source chamber 18 by way of a first inlet tube 26 and a second inlet tube 24. The first and second inlet tubes are coupled together by a metering valve or flow meter 30 so that flow of the gas into the chamber 18 may be precisely controlled. The gas from the carrier gas source 28 is applied to the chamber 18 to carry the nanoparticles 42 created by the arc plasma source down a flow tube 38. The flow tube 38 generally acts as an electrode and may comprise grounded metal conductor. A bypass tube 25 branches from the flow tube to the flow out of the flow tube 38 independent of the flow of carrier gas into the chamber 18. The bypass tube 25 leads to a metering valve 34 and then connects to an exhaust tube 27 leading to a filter 32 disposed at the end of the exhaust tube 27 to catch any nanoparticles 42 that are diverted from the flow tube 38.

A substrate electrode 40 is provided beneath the flow tube 38 and a voltage source 36 is connected between the substrate electrode 40, and the flow tube 38 to provide an electrical field therebetween. The voltage source 36 may be either positive or negative in nature, depending on the charge of the nanoparticles, so as to attract the nanoparticles to the substrate electrode 40. Supported by the substrate electrode 40 and in electrical communication with the substrate electrode 40, are nanostructures 44 to which the nanoparticles will be assembled. In one embodiment, the nanostructures 44 are carbon nanotubes (CNT) coating a substrate electrode 40 that is a perforated copper grid. The holes in the grid appear to enhance the effect of the electrical field. A gap distance (e.g., 2-0.5 mm) is maintained between the metal flow tube 38 and the substrate electrode 40 using, for example, a precision-machined ceramic spacer. The larger the gap between the flow tube 38 and the substrate electrode 40, the higher applied voltage necessary to sufficiently attract the nanoparticles 42 to the nanostructures 44.

The presence of the voltage source 36 creates an electrical field in the neighborhood of the nanostructures 44 on the substrate electrode 40. Thus, after the nanoparticles 42 flow through the flow tube 38, they are preferentially attracted to the nanostructure 44 surfaces on the substrate electrode 40. This attraction results in nanoparticle 42 decoration of the nanostructures 44, which will be discussed further below. The voltage source may provide a voltage of 2 kV-500 V depending on the gap distance. The voltage is limited only by the breakdown voltage of the carrier gas (about $3\times10^6$ V/m for dry air). Calculation from experiments show the maximum electric field near the surface of a 20-nm carbon nanotube reaches $2.45\times10^6$ V/m for a voltage source 36 of 2 kV and a gap of 2 mm.

In the absence of an electrical field, it has been determined that the nanoparticles 42 are not appreciably attracted to the nanostructures 44 and do not bond to the surfaces of the nanostructures.

Various different nanostructures 44 such as carbon nanotubes, nanorings, nanorods, and nanowires may be used in the present invention. The nanostructures 44 are produced using known methods in the relevant technological field or, alternatively, may be bought from known commercial sources, e.g., Carbon Nanotechnologies, Inc. and Alfa Aesar. Nanotubes of the invention may comprise a singular interconnected molecular sheet, e.g., single-walled nanotubes (SWNTs), or nanotubes of the invention may comprise multiple concentric molecular sheets, e.g. multi-walled nanotubes (MWNTs). Nanotubes of the present invention may comprise, but need not be limited to, carbon, boron nitride, silicon, tungsten disulfide, molybdenum disulfide, and titanium dioxide. Nanotubes of the present invention are smaller than about 1 μm in diameter, typically less than about 200 nm in diameter, and most typically less than 50 nm in diameter. Nanotubes of the present invention are longer than about 500 nm, typically longer than about 2 μm, and most typically longer than about 5 μm. Nanorods and nanowires of the invention will have dimensions similar to those disclosed above for nanotubes of the invention. Nanorods may comprise, but need not be limited to, carbon, boron nitride, silicon, tungsten disulfide, molybdenum disulfide, and titanium dioxide. Nanowires may comprise any of a number of metals which are amenable to being formed into nanowires, such as Ni, Pt, Au, Ag, or Cu.

Any of a number of nanoparticles 42 may be used for the methods of the present invention or to construct structures and devices described herein. Nanoparticles 42 may comprise, but need not be limited to, Ag, Au, Pd, Pt, Ni, Co, $TiO_2$, ZnO, $SnO_2$, $WO_3$, and combinations thereof. Nanoparticles 42 are smaller than about 1 μm in diameter, more typically smaller than about 200 nm, more typically smaller than about 50 nm, and most typically smaller than about 10 nm. Nanoparticles 42 are larger than about 1 nm, and more typically larger than about 2 nm. While nanoparticles 42 are depicted as spheres in various figures in this application, nanoparticles 42 may take any of a number of three-dimensional shapes, including, but not limited to, footballs, cylinders, obloid spheroids, or some other irregular shape, e.g., popcorn.

Figure 13:
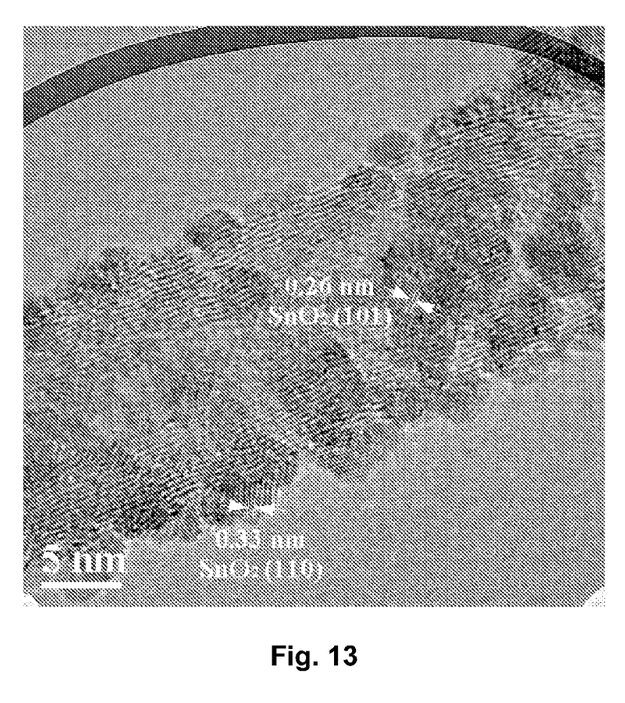
FIG. 13 is a high-resolution transmission electron microscopy image showing greater detail of the $SnO_2$-nanoparticle-coated nanotubes.

Referring now to FIG. 2, a cross-sectional simplified TEM image of a nanostructure 44 shows its surface decorated with a plurality of nanoparticles 42. The nanoparticles 42 are bonded to the exterior surface of the nanostructures 44. The adhesion between the nanoparticles 42 and the nanostructures 44 appears to be non-covalent in nature and thus preserves the $sp^2$ hybridization of the carbon atoms in that may be present in the nanostructures 44. By maintaining this $sp^2$ hybridization, the unique intrinsic properties of the nanostructures 44 are preserved. The bonding between the nanostructures 44 and nanoparticle 42 may provide for good electrical conduction between the two. An actual TEM image of a nanostructure decorated with $SnO_2$ nanoparticles is shown in FIG. 13.

The nanoparticles 42 are generally evenly spaced across the external surface of the nanostructure 44 because of the electrical charge carried on each of the nanoparticles 42 which causes them to mutually repel one another leading to a minimum energy configuration of substantially uniform distribution. The average separation of the nanoparticles 42 bonded to the external surfaces of the nanostructures 44 can be controlled by adjusting the assembly conditions. For example, adjusting the duration of the flow of nanoparticles 42 over the substrate electrode 40 will control the packing density of the nanoparticles 42 on the nanostructures 44 as the packing density increases with increased assembly time. If the assembly time is sufficiently long, the entire surface of the nanostructure 44 may be coated with nanoparticles 42. By controlling the packing density it is possible to prepare closely-packed nanoparticles on nanostructures as is shown in FIG. 13.

Figure 3:
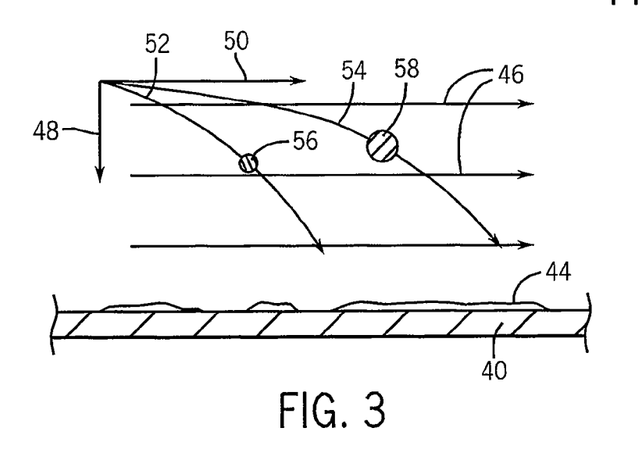
FIG. 3 is a cross-sectional elevation view of the flow of nanoparticles over the nanostructures per FIG. 1 showing the perpendicular forces of gas flow and electrostatic attraction that can be used to sort nanoparticle size.

Referring now to FIG. 3, controlling the flow rate of the nanoparticles 42 or the strength of the electrical field will control the size of the nanoparticles 42 assembled on the nanostructures 44. As the nanoparticles 42 approach the substrate electrode 40, they are held in a laminar flow represented by flow lines 46 applying an airflow force 50 on the nanoparticles 56 and 58 that is dependant on the size of the nanoparticles 56 and 58. In contrast, an electrostatic force 48 perpendicular to the airflow force 50 and toward the substrate is dependent on the charge of the nanoparticles 56 and 58 which will be largely independent of their size. These competing forces create trajectory lines 52 and 54 that sort nanoparticles 42 of different sizes. Trajectory line 52 is traveled by representative small nanoparticle 56 and depicts the result of a proportionally larger electrostatic force 48 than airflow force 50 while trajectory line 54 is traveled by relatively larger nanoparticle 58 represents a proportionally smaller electrostatic force 48 than airflow force 50. Larger nanoparticles 58 tend to be carried along further by the airflow force 50 due to their size relative to that of the smaller nanoparticles 56 allowing size distribution to be controlled. Nanoparticle size can affect the properties of the nanoparticles 42.

To the extent that the amount of charge can be controlled on different nanoparticles 42, this same effect may be used to sort nanoparticle materials or provide different size ratios among nanoparticles 42 of different materials.

Nanoparticles 42 reaching the nanostructures 44 are selected through their electrical mobility, the ability of a particle to move in an electrical field, characterized by the following equation: $Z_p = v_p/E = neC_c/3\pi\mu D_p$, wherein $v_p$ is the nanoparticle 42 velocity along electric field lines, E is the electrical field, n is the number of elementary charges carried by nanoparticles, e is the elementary charge, $C_c$ is the Cunningham slip correction factor, $D_p$ is the diameter of the nanoparticles, and $\mu$ is the flow viscosity. The electric field need not be homogenous but can be further altered to control the distribution of the particles for example with electrode shapes, shields or photoelectric dissipation. Some size selection is also intrinsic to the process of generating and conveying the aerosolized nanoparticles 42.

It is also possible to produce decorated nanostructures 44 with nanoparticles 42 of varying composition by performing multiple ESFDA treatments to the nanostructures 44 and by varying the precursor materials 22 between ESFDA treatments. It is also possible to produce a mixture of nanoparticles 42 by using specially-chosen mixtures of precursor materials 22 in a single ESFDA treatment. Alternatively, it is possible to use multiple ESFDA devices 10 to simultaneously produce and deposit nanoparticles 42 of desired composition and size.

Figure 4:
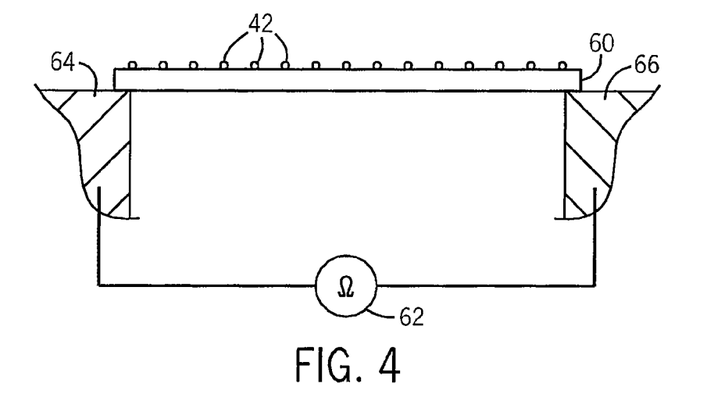
FIG. 4 is an elevation view of a nanotube disposed between electrodes and having reactive nanoparticles on its surface to provide a novel sensing electrode.

Referring now to FIG. 4, the present invention may be used to construct a novel device in which a single nanotube 60 is disposed between a first electrode 64 and a second electrode 66. An ohmmeter 62 or similar current sensitive device is placed between the two electrodes to measure the resistance of the nanotube 60. Nanoparticles 42 are lined up across the surface of the nanotube 60 using the assembly procedure discussed herein. Alternatively, the nanotube 60 could be replaced by another type of conductive nanostructure 44.

Figure 10:
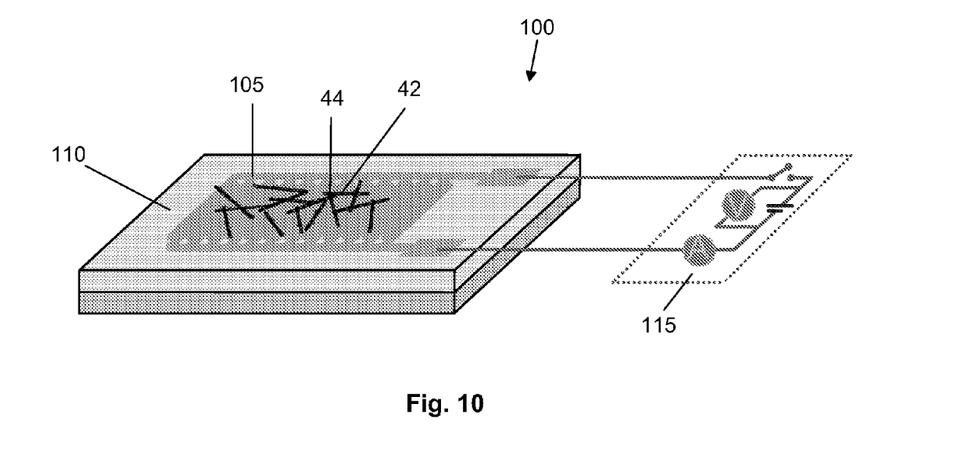
FIG. 10 is a schematic representation of an ambient-temperature gas sensor constructed of interdigitated electrodes and nanoparticles deposited upon nanotubes, wherein the interdigitated electrode is operatively connected to a meter.

Using ESFDA device 10 it is possible to construct a device suitable for the detection of chemical species in the ambient air, e.g., a gas sensor. Referring to FIG. 10, gas sensor 100 is constructed by affixing one or more electrodes 105 to a substrate 110, wherein one or more electrodes 105 are connected to a meter 115 capable of measuring the an electrical characteristic of electrodes 105, or between electrodes 105. The electrical characteristics detectable by meter 115 may include, but are not limited to, conductance, capacitance, potential, resistance, reluctance, inductance, magnetic field, and magnetic flux. Nanostructures 44 are then deposited on the one or more electrodes 105 using ESFDA or by other know means, for example, suspending nanostructures 44 in a solvent solution and then evaporating the solvent to leave nanostructures 44 deposited upon one or more electrodes 105. Nanoparticles 42 are subsequently deposited (decorated) upon nanostructures 44 using the ESFDA techniques disclosed herein. Optionally, nanostructures 44 may be annealed to one or more electrodes 105 prior to depositing nanoparticles 42 on nanostructures 44. Depending upon the size and composition of nanoparticles 42, gas sensor 100 can be fabricated to be sensitive to a variety of gasses, and to have a linear response over a desired concentration range. Gas sensor 100 may be sensitive to a number gasses, including toxic and flammable gasses, which may include, but are not limited to $H_2$, $NO_2$, $CO$, $NH_3$, $H_2S$, and $CH_4$.

Figure 11:
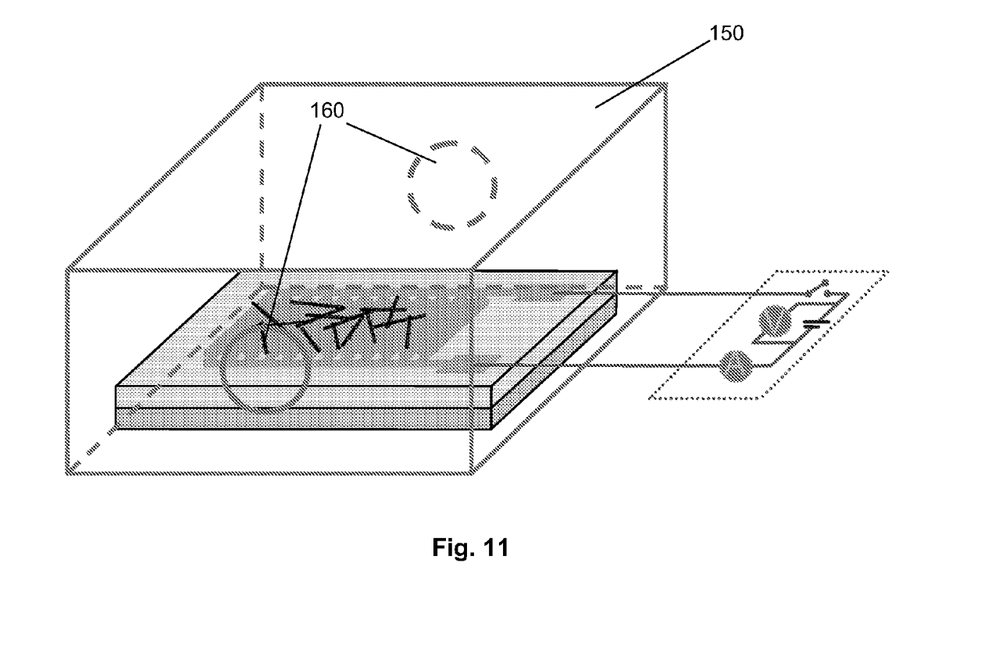
FIG. 11 is a schematic representation of an ambient-temperature gas sensor optionally housed in a container having sidewalls allowing for gaseous communication between the ambient environment and the ambient-temperature gas sensor.

Gas sensor 100 may be produced individually, or gas sensor 10 may be mass produced, on semiconductor microchips for example, using known techniques of photolithography in combination with the ESFDA techniques of the present invention. In one commercial embodiment, gas sensor 100 may employ container 150 to protect gas sensor 100 from mechanical shock and to provide electrical insulation. Container 150 may optionally have openings 160 to allow gaseous communication between gas sensor 100 and the ambient environment outside container 150. In a separate embodiment, a plurality of gas sensors 100 may be arrayed on substrate 110 to facilitate the fabrication of a single device being sensitive to a variety of gasses and having a linear response to the gases over a broad concentration range. Such a device may further comprise a plurality of meters 115 interfaced to a circuit to allow real-time detection of complicated gaseous environments. In another embodiment the array, and the various meters, may be incorporated into a single component, such as a dual inline package, quad flat package, plastic leaded carrier, small outline package, etc., thus providing a low power, sensitive, gas analyzer that is responsive to a plurality of gasses.

Gas sensor 100, formed with the techniques of the present invention are easily-fabricated and may deliver a linear response to gasses over a wide variety of gas sensor 100 temperatures. Because gas sensor 100 delivers a linear response over a wide range of temperatures, it is not necessary to provide an independent heat source for gas sensor 100. The lack of an independent heat source both simplifies fabrication of gas sensor 100 and reduces the power consumption of gas sensor 100. While gas sensor 100 functions optimally at room temperature, i.e. about 25° C., gas sensor 100 will typically provide a linear response over the temperature range of about −20° C. to about 300° C., more typically from about 0° C. to about 200° C., and most typically from about 15° C. to about 30° C.

Figure 6:
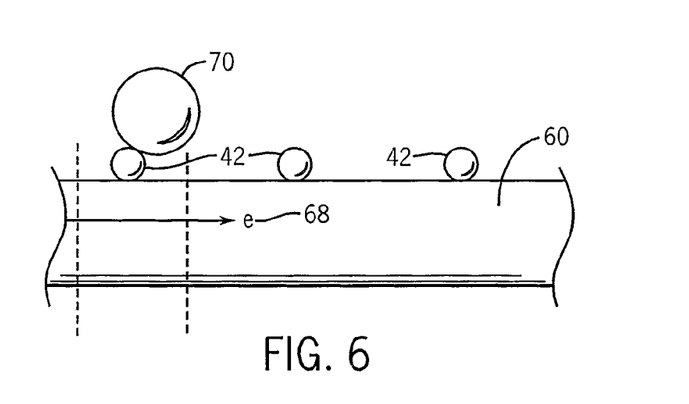
FIG. 6 is a fragmentary view similar to that of FIGS. 4 and 5 showing a sensor in which nanoparticles attracting environmental agents, affect current flow in the underlying nanotube to create a sensor.

As shown in FIG. 6, the nanoparticles 42 may be selected to attract other particles 70 in the environment and bond to them. This bonding creates a region of increased resistance along the nanotube 60 that may be measured by the ohmmeter 62 (shown in FIG. 4) to detect the presence of the particles 70.

Figure 7:
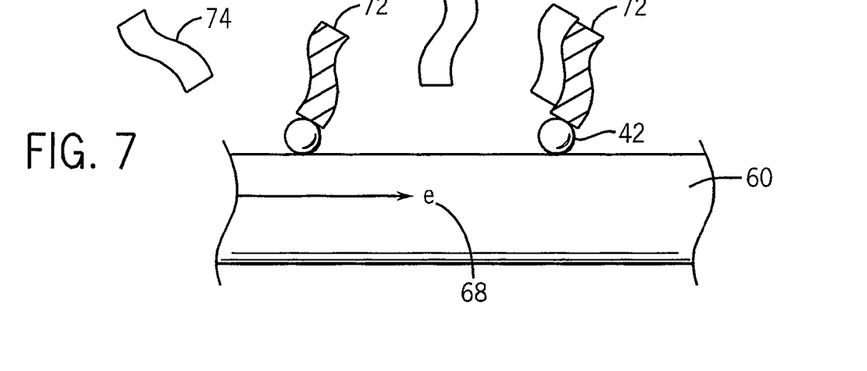
FIG. 7 is a fragmentary view similar to that of FIG. 6 showing the same principle used to detect complex molecules such as DNA or RNA.

As shown in FIG. 7, in an alternative embodiment, strands of nucleotides 72 may be attached to the nanoparticles (before or after assembly) to hybridize with complimentary nucleotides 74 in the environment. Again, the result of this bonding of nucleotides 74 may be detected in changes in the flow of electrons 68 within the nanotube 60 near the bonded nucleotides 72. This particular embodiment is useful in the field of biosensors sensitive to the presence of a particular biological agent. The nucleotide 72 is selected to bond only to the particular agent to be detected.

Figure 8:
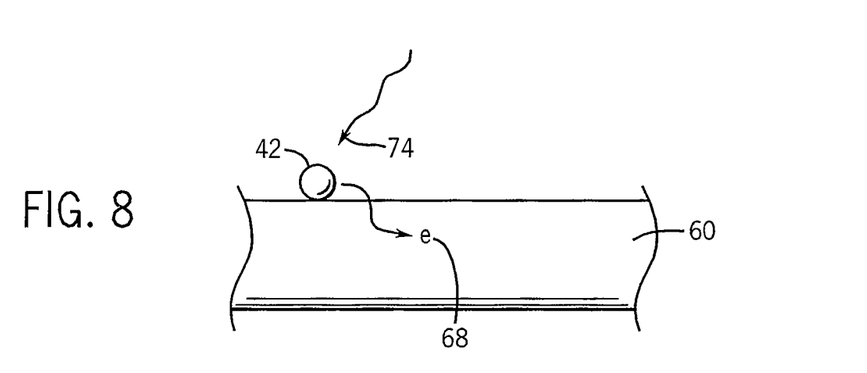
FIG. 8 is a fragmentary view similar to that of FIG. 7 showing the structure used as a photocell or light sensor by providing a closely coupled path between a photoelectric material and a conductive wire.

Referring to FIG. 8, a photoelectric nanoparticle 42 attached to the surface of a carbon nanotube 60 may be struck by a light ray 74 to eject electrons 68 collected by the nanotube 60 to create an improved photocell or photo sensor.

Figure 5A:
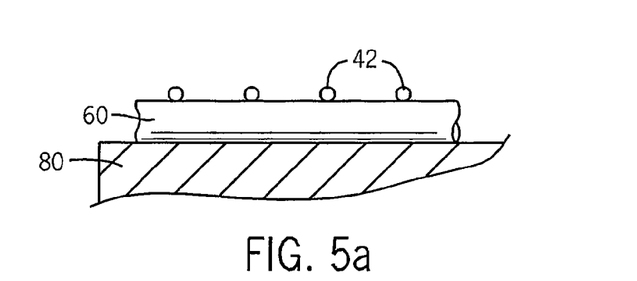
FIGS. 5a and 5b are elevation fragmentary views of an assembled nanotube and nanoparticles showing steps of destroying the nanotube to transfer the ordered nanoparticles to a secondary substrate.
Figure 5B:
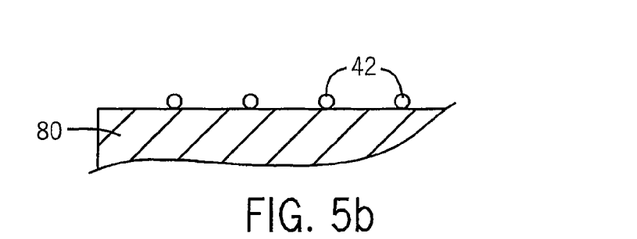

Referring now to FIGS. 5a and 5b, a carbon nanotube 60 is placed on the surface of a substrate 80. Using the disclosed assembly procedure, nanoparticles 42 are lined up across the surface of the nanotube 60. By applying a high voltage or heat or oxidizing chemical to the nanotube 60, the nanotube 60 can be destroyed leaving behind only the nanoparticles 42 which remain lined up in a row on the substrate as shown in FIG. 5b. This technique can be used with conductive or semiconductive nanoparticles 42 to create fine conductive or semiconductive paths (for example, for integrated circuits) or to create fiducial marks on the substrate 80 for studies of microscopic strain or the like.

Figure 9:
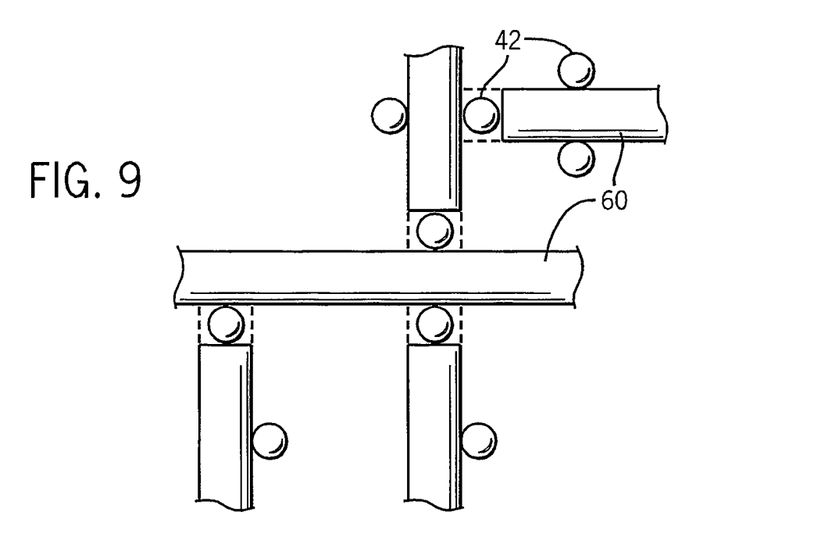
FIG. 9 is a fragmentary elevation view of a complex nanotube structure generated by seeding nanotubes with catalyst nanoparticles to create sites from which other nanotubes can be grown.

Referring now to FIG. 9 the nanoparticles 42 may be a catalyst that is used to grow additional nanotubes 60 branching from the nanotubes 60 on which the nanoparticles 42 were originally deposited. The resultant structure may have a relatively large surface area while having a relatively small volume and may, in turn, be coated with different nanoparticles 42 to provide for catalytic structures, photocells, or filters or the like.

EXAMPLE

Ambient-Temperature Gas Sensor Employing Multi-Wall Carbon Nanotubes (MWCNTs) and $SnO_2$ Nanoparticles Gold interdigitated electrodes (IDEs) with a finger width and an inter-finger spacing of 1 μm were fabricated by an e-beam lithography process, using known techniques. Multi-walled carbon nanotubes (MWCNT) (20 nm O.D., 5-20 μm long) purchased from Alpha Aesar (Ward Hill, Mass.) were then uniformly dispersed in ethanol and formed into a suspension with ultrasonication. A few drops of the MWCNT-ethanol suspension were deposited onto the gold IDEs. Upon evaporation of the ethanol, a sparse network of MWCNTs was left on the gold IDEs. The network spanned across neighboring fingers and closed the sensor circuit. The coverage density of MWCNTs on the interdigitated electrode can be varied by simply adjusting the concentration of the MWCNT-ethanol suspension. The MWCNTs on the gold IDEs were next annealed in an argon flow at 200° C. for one hour to remove remanent ethanol. This annealing step also improved the MWCNT-Au contact as indicated by increased sensor conductance.

Next, a mini-arc plasma source was used to synthesize aerosol tin oxide nanoparticles through physical vapor deposition, as described above. The thermal energy from the arc discharge caused the solid tin powders placed in the reactor to melt and vaporize. The tin vapor was quenched by a cold nitrogen flow to nucleate tin nanoparticles, which were subsequently oxidized to form $SnO_2$ nanoparticles in a pure oxygen flow. Some of the $SnO_2$ nanoparticles from the mini-arc reactor were electrically charged by the arc plasma or through thermionic emission. The charged tin oxide nanoparticles were subsequently assembled onto the MWCNT on the sensor substrate using the ESFDA technique described above. The charged nanoparticles were carried into a gap formed between the grounded tubing for the nanoparticle delivery and the electrically-biased CNTs on the interdigitated electrode. The electric field near the MWCNT was significantly enhanced due to its small diameter and the charged $SnO_2$ nanoparticles were attracted to the external surface of oppositely-charged MWCNTs via electrostatic force.

Figure 12:
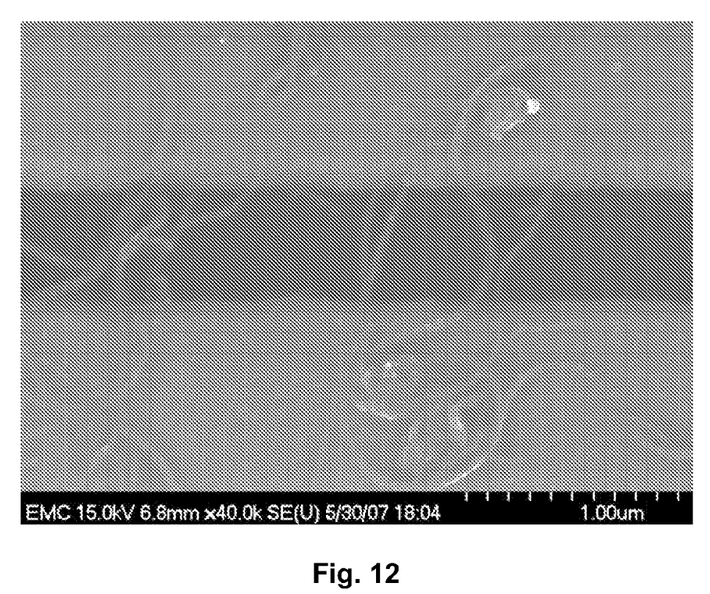
FIG. 12 is a scanning electron micrograph of an ambient-temperature gas sensor detailing $SnO_2$-nanoparticle-coated nanotubes spanning the interdigitated electrodes (top and bottom).

FIG. 12 shows a scanning electron micrograph (SEM) image of several $SnO_2$ nanoparticle-covered MWCNTs spanning the gap between the gold IDEs. FIG. 13 shows a high-resolution transmission electron microscopy (HRTEM) image of one of the $SnO_2$ nanoparticle decorated MWCNTs of the sensor. Discrete $SnO_2$ nanoparticles of about 2 to 3 nm in size are uniformly decorated on the external surface of the MWCNT. Lattice spacing measurements of the nanoparticles gave recurrent values of 0.33 nm and 0.26 nm, which correspond to the lattice spacings of rutile $SnO_2$ from (110) and (101) reflections, respectively. Such small size and narrow distribution of $SnO_2$ nanoparticles on the CNT are attributed to the known intrinsic nanoparticle size selection resulting from the ESFDA process.

The performance of the ambient-temperature gas sensor was characterized at room temperature against low-concentrations of $NO_2$, $H_2$, and CO in dry air. Gases were detected by measuring the change in the electrical conductance of the ambient-temperature gas sensor as a function of time as the sensor was exposed to various gaseous environments. For test purposes, the ambient-temperature gas sensor was mounted in an air-tight sensor test chamber with electrical feedthroughs and an ability to change the interior gas composition. Conductance measurements were carried out using a Keithley 2602 source meter by applying a constant dc voltage to the ambient-temperature gas sensor while simultaneously monitoring the variation in the current when the ambient-temperature gas sensor was periodically exposed to clean air and when the ambient-temperature gas sensor was challenged with gases.

Figure 14:
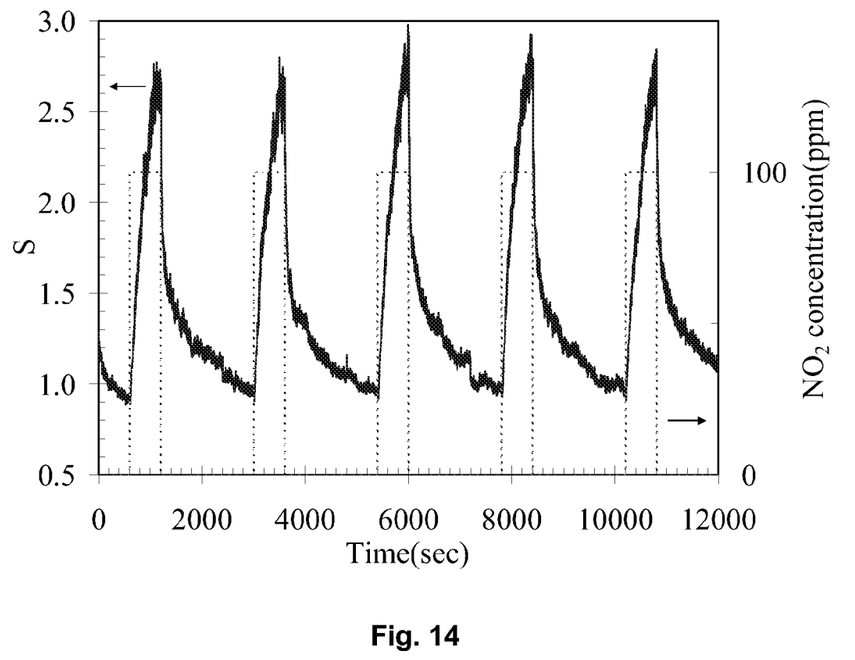
FIG. 14 shows the response of an ambient-temperature gas sensor of the invention to $NO_2$.

FIG. 14 shows the dynamic response of the ambient-temperature gas sensor to repeated challenges of 100 ppm $NO_2$, performed at room temperature, and without application of additional heat to the ambient-temperature gas sensor. As is indicated by the dotted lines, the ambient-temperature gas sensor was repeatedly exposed to clean air flow (2 L/m) for 10 min. to record a base value of the sensor resistance; 100 ppm $NO_2$ diluted in air (2 L/m) for 10 min. to register a sensing signal; and then clean air flow (2 L/m) for 20 min to recover the device. Five such cycles were repeated as shown in FIG. 14 and the sensing behavior appeared fairly reproducible. The average sensitivity S, which is defined as the ratio of the sensor resistance in air to that in the challenging gas, was about 2.8; the response time constant was about 4.5 min; and the recovery time constant was about 2.5 min.

Figure 15:
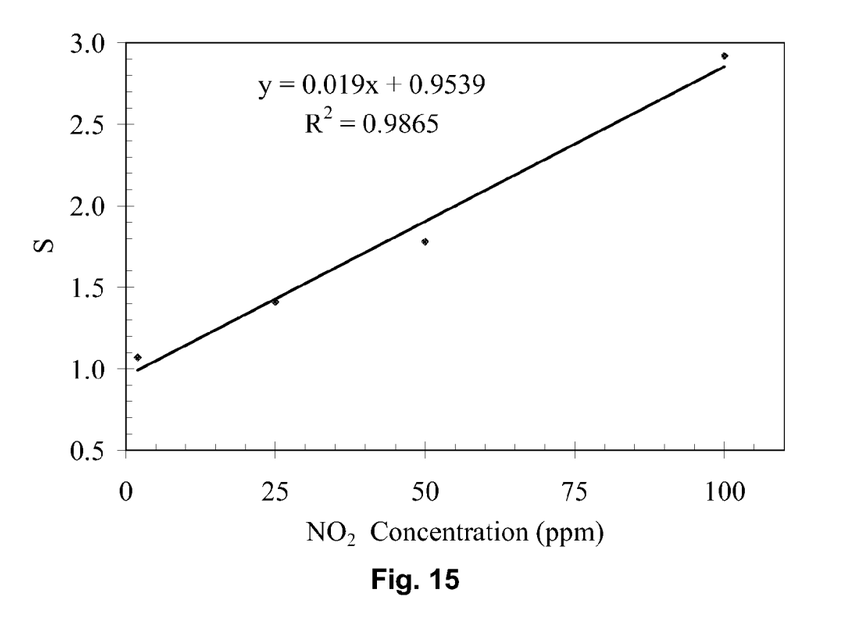
FIG. 15 shows the linearity of the response of an ambient-temperature gas sensor of the invention.

The dependence of the sensor response on the $NO_2$ concentration was also investigated. FIG. 15 compares the sensor responses to 100, 50, and 25 ppm $NO_2$, showing higher sensor sensitivity S with increasing $NO_2$ concentration. As can be seen from FIG. 15, the response is quite linear with increasing $NO_2$ concentration.

Figure 16:
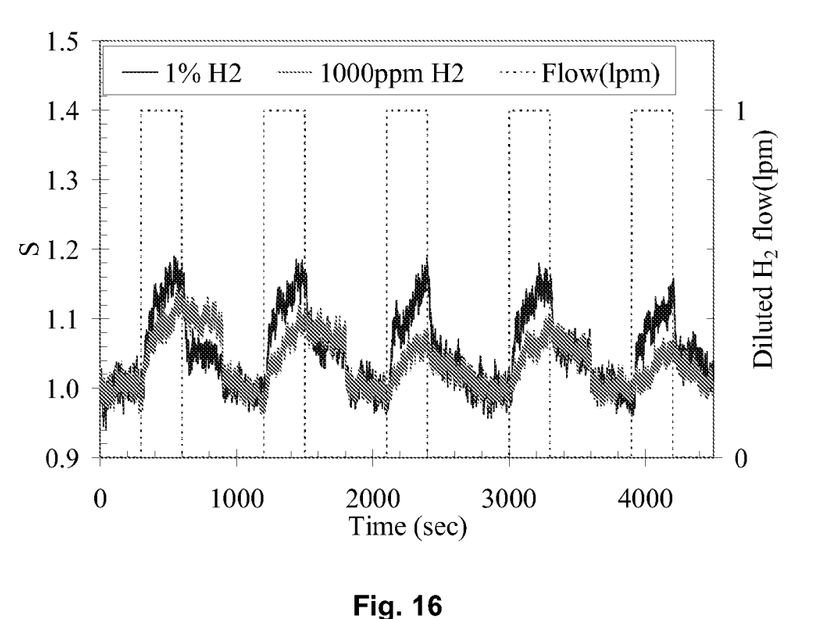
FIG. 16 shows the response of an ambient-temperature gas sensor of the invention to $H_2$.

The same ambient-temperature gas sensor exhibited sensitivity to $H_2$ and CO, although bare MWCNTs are insensitive to these gaseous molecules. FIG. 16 shows the room-temperature sensing performance of the ambient-temperature gas sensor for the detection of 1% and 1000 ppm $H_2$ diluted in air.

Figure 17:
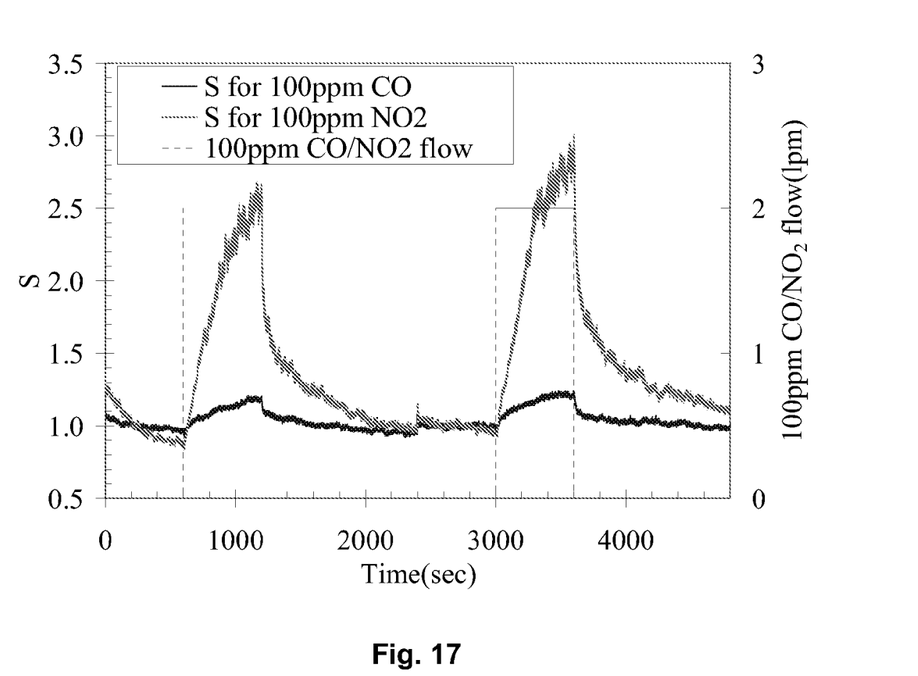
FIG. 17 shows the response of an ambient-temperature gas sensor of the invention to CO and $NO_2$.

For 1000 ppm $H_2$, the average sensitivity was about 1.10; the response time constant was about 4.2 min; and the recovery time constant was about 4.5 min. FIG. 17 shows the room-temperature sensing performance of the ambient-temperature gas sensor for the detection of 100 ppm CO diluted in air, and the room-temperature sensing performance of the ambient-temperature gas sensor for the detection of 100 ppm of $NO_2$ for comparison. For CO, the sensitivity was about 1.11; the response time constant was about 3.7 min; and the recovery time constant was about 4.6 min.

Thus, the present invention provides methods for the fabrication of nanomaterials, including gas sensors. Various alternatives are contemplated as being within the scope of the following claims, particularly pointing out and distinctly claiming the subject matter regarded as the invention.

What is claimed is:

1. An ambient-temperature gas sensor, comprising:
    (a) one or more electrodes, formed on a substrate and adapted to be operatively connected to a meter to measure an electrical characteristic between the electrodes;
    (b) one or more nanostructures in contact with the one or more electrodes; and
    (c) one or more nanoparticles deposited on the nanostructures;
    wherein the sensor is operative for a temperature range from about 0° C. to about 200° C.; and wherein the nanoparticles are discrete, non-agglomerated three-dimensional nanoparticles.

2. The ambient-temperature gas sensor of claim 1, wherein the electrode is microfabricated.

3. The ambient-temperature gas sensor of claim 2, wherein the electrode comprises Au, Ag, Pt, Cu, or a combination thereof.

4. The ambient-temperature gas sensor of claim 3, wherein the electrode is an interdigitated electrode (IDE).

5. The ambient-temperature gas sensor of claim 1, wherein the nanostructures are nanotubes, nanorings, nanorods, nanowires, or combinations thereof.

6. The ambient-temperature gas sensor of claim 5, wherein the nanostructures are nanotubes.

7. The ambient-temperature gas sensor of claim 6, wherein the nanostructures are multi-walled carbon nanotubes.

8. The ambient-temperature gas sensor of claim 1, wherein the nanoparticles comprise Ag, Au, Pd, Pt, Ni, Co, $TiO_2$, ZnO, $SnO_2$, $WO_3$, or combinations thereof.

9. The ambient-temperature gas sensor of claim 8, wherein the nanoparticles comprise rutile $SnO_2$.

10. The ambient-temperature gas sensor of claim 1, wherein the nanoparticles are less than about 50 nm in diameter.

11. The ambient-temperature gas sensor of claim 10, wherein the nanoparticles are less than about 10 nm in diameter.

12. The ambient-temperature gas sensor of claim 1, further comprising a housing for the sensor, the housing having sidewalls allowing for gaseous communication between the ambient environment and the sensor.

13. The ambient-temperature gas sensor of claim 1, wherein the sensor is formed as a semiconductor microchip.

14. An array of ambient-temperature gas sensors of claim 1, comprising a plurality of ambient-temperature gas sensors of claim 1.

15. The array of ambient-temperature gas sensors of claim 14, wherein one or more of the ambient-temperature gas sensors of the plurality of ambient-temperature gas sensors comprise nanoparticles of differing composition.

16. A method of detecting a gas, comprising:
    (a) providing an ambient-temperature gas sensor according to claim 1;
    (b) introducing a gas; and
    (c) monitoring a change in an electrical characteristic between the one or more electrodes as a function of time.

17. The method of detecting a gas of claim 16, wherein the change in an electrical characteristic between the one or more electrodes as a function of time indicates the presence of a gas.

18. The method of detecting a gas of claim 16, wherein the electrical characteristic is selected from the group consisting of conductance, capacitance, potential, resistance, and inductance.

19. The method of detecting a gas of claim 16, wherein the ambient-temperature gas sensor is maintained from about 15° C. to about 30° C.

20. The method of detecting a gas of claim 16, wherein the ambient-temperature gas sensor is enclosed in a container which allows for gaseous communication between the ambient environment and the ambient-temperature gas sensor.

21. The method of detecting a gas of claim 16, wherein the gas is flammable.

22. The method of detecting a gas of claim 16, wherein the gas is toxic.

23. The method of detecting a gas of claim 16, wherein the gas is selected from the group consisting of $H_2$, $NO_2$, CO, $NH_3$, $H_2S$, and $CH_4$.

24. The ambient-temperature gas sensor of claim 1, wherein the nanostructures comprise carbon.

25. The ambient-temperature gas sensor of claim 1, wherein the nanostructures are single-walled carbon nanotubes.

* * * * *